United States Patent [19]

Steinhaus et al.

[11] Patent Number: 5,562,712
[45] Date of Patent: Oct. 8, 1996

[54] MINUTE VOLUME RATE-RESPONSIVE PACEMAKER USING DUAL UNIPOLAR LEADS

[75] Inventors: Bruce Steinhaus, Arker; Albert Dawson, Littleton; Richard Lu, Highlands Ranch, all of Colo.

[73] Assignee: Dow Corning Corporation, Midland, Mich.

[21] Appl. No.: 345,651

[22] Filed: Nov. 25, 1994

[51] Int. Cl.⁶ .................................................. A61N 1/368
[52] U.S. Cl. ............................................ 607/20; 128/734
[58] Field of Search .......................... 607/20, 24; 128/734

[56] References Cited

U.S. PATENT DOCUMENTS

| | | | |
|---|---|---|---|
| 4,596,251 | 6/1986 | Plicchi et al. | 607/20 |
| 4,702,253 | 10/1987 | Nappholz et al. | 607/20 |
| 4,790,318 | 12/1988 | Elmqvist et al. | 607/20 |
| 4,901,725 | 2/1990 | Nappholz et al. | 607/20 |
| 5,201,808 | 4/1993 | Steinhaus et al. | 607/20 |
| 5,314,449 | 5/1994 | Lindgren | 607/24 |
| 5,355,894 | 10/1994 | Sivard | 607/20 |

*Primary Examiner*—William E. Kamm
*Assistant Examiner*—Kennedy J. Schaetzle
*Attorney, Agent, or Firm*—Roger E. Gobrogge

[57] ABSTRACT

A rate-responsive pacemaker including a pulse generator for providing pacing current pulses at a controlled rate and two unipolar leads are provided. The pulse generator also applies a measuring current between one of the electrodes and a reference point in the pacemaker. The impedance between the other electrode and the reference point is measured across a lung of the patient. The impedance of the patient varies as a function of patient's pleural pressure, and therefore, the impedance thus represents the patient's minute volume. The rate of pacing is automatically adjusted in response to changes in the patient's minute volume.

21 Claims, 3 Drawing Sheets

MINUTE VOLUME RATE-RESPONSIVE PACEMAKER USING DUAL UNIPOLAR LEADS

BACKGROUND OF THE INVENTION

A. Field of Invention

This invention relates generally to a rate-responsive pacemaker, and, in particular, to a rate-responsive pacemaker in which the rate control parameter is minute volume and the sensing is accomplished by dual chamber unipolar leads.

B. Description of the Prior Art

U.S. Pat. No. 4,702,253, entitled "Metabolic-Demand Pacemaker and Method of Using the Same to Determine Minute Volume", which issued Oct. 27, 1987, to Nappholz et al., discloses a rate-responsive pacemaker which employs minute volume as a rate control parameter. Minute volume is a measure of the amount of air inspired by a person as a function of time. The greater the amount of air inspired, the greater the need for a higher heart pacing rate. The pacemaker of the aforesaid patent (hereinafter called "the '253 pacemaker") measured minute volume by providing a three-electrode lead which employs one electrode referenced to a pacemaker case to sense heart signals and pace the patient's heart in the conventional manner and which employs the remaining two electrodes to perform the minute volume measurement. The two electrodes for measuring minute volume were located in the superior vena cava blood vessel and/or in a cardiac chamber in the vicinity of the patient's pleural cavity. The '253 pacemaker periodically applied current pulses between one of the electrodes and the pacemaker case, and measured the voltage which resulted from the applied current between the other electrode and the pacemaker case. The measured voltage was a function of the blood impedance in the vessels in and around the pleural cavity which, in turn, depended upon the pleural pressure. The '253 pacemaker determined the minute volume by monitoring the variation in the impedance measurement.

One problem with the '253 pacemaker is that it requires a lead having at least three electrodes while the industry has standardized unipolar (single electrode) and bipolar (dual electrode) leads. There are many patients with implanted old pacemaker systems having unipolar and bipolar leads, and if a three-electrode lead is required for a new pacemaker, then the new pacemaker cannot readily replace an old pacemaker and use the old leads. Furthermore, there are physicians who like the feel of the existing, standard leads they have been using in the past, and one factor which weighs against implanting a rate-responsive pacemaker might be that it requires a new lead type having a new feel.

U.S. Pat. No. 4,901,725, entitled "Minute Volume Rate-Responsive Pacemaker", which issued Feb. 20, 1990, to Nappholz et al., disclosed an improved minute rate-responsive pacemaker (hereinafter called "the '725 pacemaker") which can be used with a conventional bipolar lead. This bipolar lead had two electrodes for sensing and pacing the heart. In the '725 pacemaker, the standard ring electrode was used additionally to apply a current which flows to the pacemaker case. The tip electrode was used to measure the blood impedance between the tip and the case in response to the current pulse applied through the ring electrode. The '725 pacemaker utilized the measured blood impedance to derive an appropriate pacing rate.

Although the '725 pacemaker used a bipolar lead which is standard in cardiac pacing, it had a limitation in that this pacemaker could not be used in the many patients who had previously implanted unipolar leads. Unipolar leads, which have a single tip electrode, are also standard in the art of cardiac pacing. If a bipolar lead is required when a patient has a new pacemaker implanted, then a non-rate-responsive pacemaker that is connected to a unipolar lead cannot be replaced by a rate-responsive pacemaker embodying the invention of the '725 pacemaker simply by exchanging pacemakers and using the same lead.

Previous attempts have been made to perform minute volume rate-responsive pacing in a pacemaker using unipolar leads. These attempts failed, primarily because the blood impedance signal measured from unipolar leads was too weak in comparison to system noise and other unwanted signals present. Additionally, U.S. Pat. No. 5,201,808 (hereinafter called "the '808 pacemaker") entitled "Minute Volume Rate-Responsive Pacemaker Employing Impedance Sensing on a Unipolar Lead," which issued Apr. 13, 1993, to Steinhaus et al., discloses calculating minute volume through the use of one unipolar lead. The '808 pacemaker did not measure impedance between the tip electrode and the case as was previously done in prior art devices, but instead the impedance measurement was taken between the input of the lead from the pacemaker and the pacemaker case. Therefore the pacemaker senses the impedance of the body tissues along the entire length of the lead by providing a high frequency exultation to the lead. Therefore the pacemaker requires very complex circuitry.

Accordingly, it is desirable to develop a minute volume rate-responsive pacemaker device for use with conventional unipolar leads that does not significantly increase the complexity of the circuitry involved, and does not increase the cost of manufacture of the device.

SUMMARY OF THE INVENTION

Generally speaking, in accordance with the present invention, a rate-responsive pacemaker includes a pulse generator for providing pacing current pulses at a controlled rate. A first unipolar lead is coupled to the pulse generator and has an electrode located at its distal end to sense and pace the atrium. A second unipolar lead coupled to the generator is used for sensing and pacing the ventricle. A circuit is provided for applying impedance measuring current pulses between one of these electrodes and a reference point, such as the pacemaker case. A second circuit is provided for measuring the voltage drop between the other electrode and the reference point across a lung. The patient's minute volume is calculated from the measurement thus obtained, and the pulse generator rate is changed in accordance with the patient's minute volume.

It is an object of the present invention to provide a pacemaker utilizing two unipolar leads provided in a patient's atrium and ventricle, such that a rate-responsive pacemaker can be used without the need to replace a pair of unipolar leads with a bipolar lead.

Another object of the present invention is to provide a minute volume rate-responsive pacemaker that is capable of operating with two unipolar leads, without requiring undue complexity in the pacemaker.

Still other objects and advantages of the present invention will be apparent from the following description of the invention.

BRIEF DESCRIPTION OF THE DRAWINGS

For a fuller understanding of the invention, reference is made to the following description, taken in connection with the accompanying drawings, in which.

DETAILED DESCRIPTION

Figure 1:
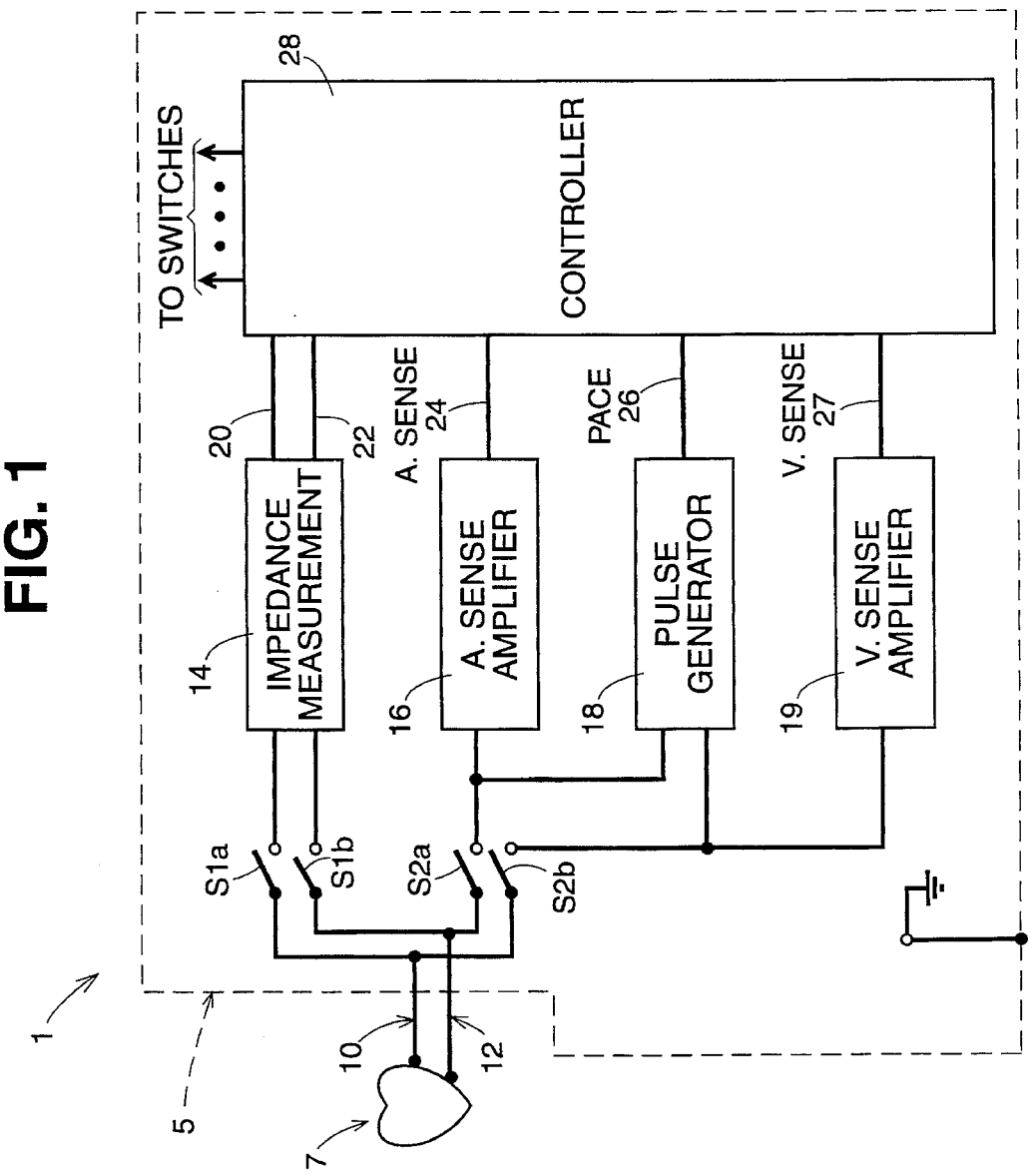
FIG. 1 shows a block diagram of the illustrative embodiment of the invention.

FIG. 1 shows a block diagram for a pacemaker 1. All pacemaker logic is disposed in a case 5 and under the control of a controller 28. The controller operates various switches in the pacemaker, of which only two pairs, S1a, S1b, S2a, S2b, are shown for the sake of clarity.

Impedance measurements are made by circuit 14, in response to a request signal to measure impedance issued by controller 28 to line 20, by closing switches S1a and S1b, and opening switches S2a and S2b. A voltage signal indicative of the measured impedance, as determined by circuit 14, is transmitted to the controller on line 22.

Figure 2:
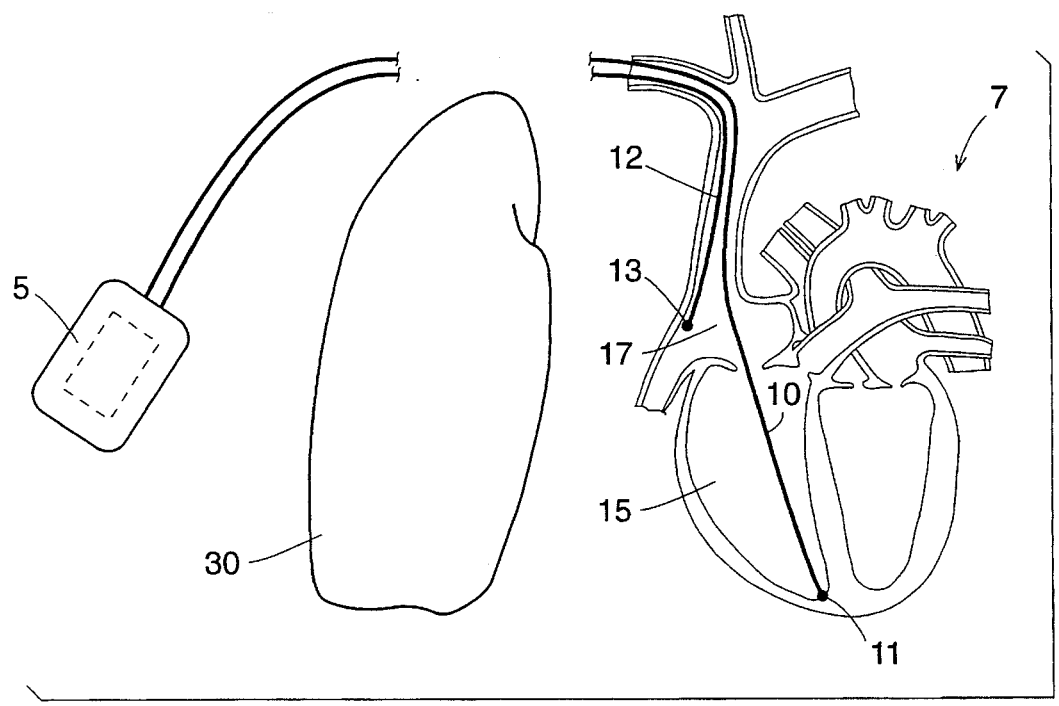
FIG. 2 shows the placement of two unipolar leads in a patient's right ventricle and right atrium.

Sensing and pacing are accomplished by closing either switch S2a or S2b and opening switches S1a, S1b, thereby connecting the atrial sense amplifier 16 or the ventricular sense amplifier 19 and pulse generator 18 to the lead 12 or 10. Briefly, as shown in FIG. 2, unipolar lead 10 extends into the ventricle 15 and is provided at its tip with an electrode 11 in the right ventricle 15 of a patient's heart 7. Similarly, unipolar lead 12 extends into the right atrium 17 and is terminated with an electrode 13.

Atrial sense amplifier 16 can sense an atrial cardiac signal on electrode 13 referenced to the pacemaker case 5. Ventricular sense amplifier 19 can sense a ventricular cardiac signal on electrode 11 referenced to the pacemaker case 5. (Various functions well known in the art, such as blanking of the sense amplifier during pacing, are not shown inasmuch as they have no bearing on the subject invention.) An atrial heartbeat, spontaneous or evoked, is sensed by amplifier 16 which, in response, sends an A. SENSE signal on A. sense line 24 to controller 28. Similarly, a ventricular heartbeat is sensed by amplifier 19 which, in response, sends a V. SENSE signal on V. sense line 27 to the controller 28. The A. SENSE signal or the V. SENSE signal initiates the loading of an initial value in a timer which determines when the next atrial or ventricular heartbeat should occur.

For pacing the heart, controller 28 sends a PACE signal on line 26 to pulse generator 18. The pulse generator 18 then sends appropriate pacing pulses to either or both unipolar leads 10, 12, depending on the mode of operation of the pacemaker.

The pacemaker makes an impedance measurement when the controller 28 sends a control signal on conductor 20 to activate impedance measurement circuit 14. As previously discussed, for this function, switches S1a and S1b close, and switches S2a and S2b open. In a somewhat preferred embodiment of the invention, impedance measurement circuit 14 applies a current to lead 12, causing current to flow between the case 5 and tip electrode 13 to the atrium 17 across lung 30. The pacemaker case 5 serves as a reference electrode for the pacemaker circuitry. The impedance measurement circuit 14 measures the blood impedance in the heart as well as an impedance across the lung 30 by determining the potential between the pacemaker case 5 and tip electrode 11 of lead 10. Advantageously, this impedance varies as a function of the patient's pleural pressure and accordingly, it provides a good indication of the minute ventilation. Circuit 14 applies a measuring current to lead 12 which may be, for example, in the range of 0.1–2.00 milliamps in the form of pulses of 1–50 microseconds. A preferred amplitude for this current is less than 1 milliamps, such as for example, 0.5 milliamps. In the preferred embodiment of the pacemaker, the impedance measurement circuit 14 applies 15 microsecond current pulses at a rate of 20 pulse per second and derives samples at the same rate. The circuit 14 sends these samples to controller 28 over line 22. The impedance measurement by circuit 14 can be performed as described in the aforementioned '253 patent.

Preferably the tip electrode 11 of lead 10 makes contact with the wall of the right ventricle 15, and tip electrode 13 of lead 12 makes contact with the wall of the right atrium 17 of the patient's heart 7. As described above, the impedance measurement reflects minute volume to a much greater extent than stroke volume or motion artifacts.

The present invention allows a minute volume rate responsive pacemaker to function through two unipolar leads. In particular, the pacemaker employs similar electronic circuitry to that disclosed in the '725 pacemaker described above. Prior to the present invention, it was believed that a bipolar or three polar lead was required to detect minute volume in the manner described above. However, the present invention provides an advancement over either the '725 pacemaker or the '808 pacemaker. The present invention allows for unipolar operation to measure minute volume.

Figure 3:
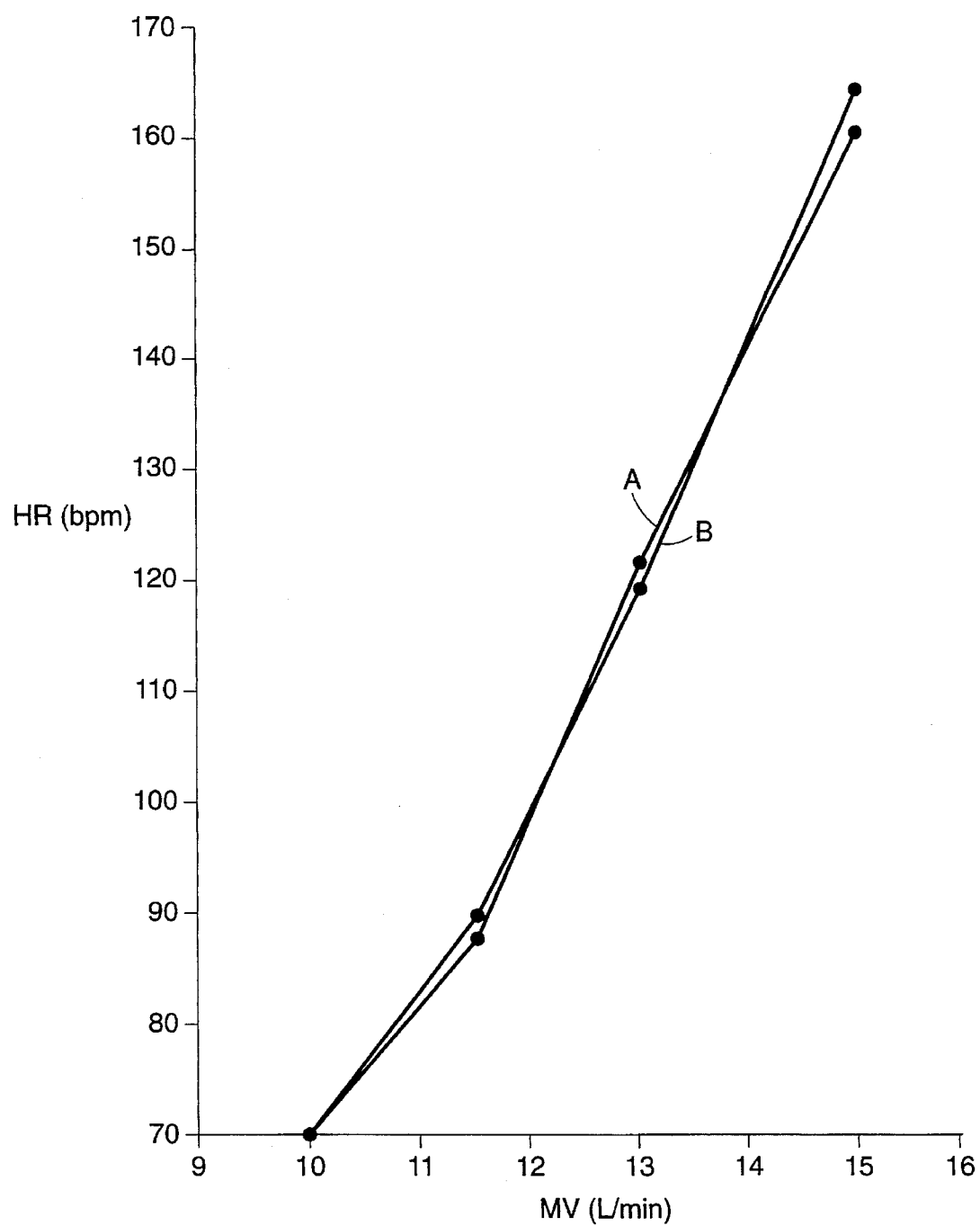
FIG. 3 shows a graph used for a comparison of the performance obtained by a bipolar ventricular lead with the performance of the dual unipolar leads of the present invention.

Experiments have been performed to compare the results obtained using of a conventional bipolar lead with dual unipolar leads in accordance with the present invention. The results of a typical experiment are shown in FIG. 3 wherein the horizontal axis indicates the minute volume (in liters/minute) obtained from changing positive pressure respirator settings and the vertical axis indicates the corresponding heart rate HR (in bpm or beats per minute) modulated by changing the minute volume. In FIG. 3, the profile A shows the performance of a standard bipolar lead in accordance with the '725 patent, while profile B shows the performance of the dual unipolar leads. It is clear from the Figure that the results obtained for the two types of leads are substantially identical.

Obviously numerous modifications may be made to this invention without departing from its scope as defined in the appended claims. For example, the current could be injected by the impedance measurement circuit 14 into lead 10 and the voltage indicative of the impedance could be measured between electrode 13 and case 30.

What is claimed is:

1. A rate-responsive pacemaker system comprising:
   pulsing means for providing pacing pulses at a controlled rate;
   first and second unipolar leads, each having an electrode for coupling respectively to an atrium and a ventricle of a patient;
   at least one of said unipolar leads being coupled to said pulsing means for delivering pacing pulses to said patient's heart;
   means for applying a measuring current between one of said electrodes and a reference point;
   means for measuring the impedance between the other of said electrodes and said reference point in response to the application of said measuring current pulse between said one electrode and said reference point, wherein said impedance varies as a function of the patient's pleural pressure; and means for changing said controlled rate in accordance with said impedance.

2. The rate-responsive pacemaker system of claim 1 wherein said measuring current applying means applies said current to the unipolar lead that is coupled to the atrium of the patient's heart.

3. The rate-responsive pacemaker system of claim 4 wherein said impedance measuring means is coupled to the unipolar lead that is coupled to the ventricle of the patient's heart.

4. The rate-responsive pacemaker system of claim 2 wherein said measuring current is less than one milliamp.

5. The rate-responsive pacemaker of claim 2 wherein said measuring current is 0.1–2.0 milliamps.

6. The rate-responsive pacemaker system of claim 5 wherein said measuring current is applied in pulses.

7. The rate-responsive pacemaker system of claim 1 wherein said reference point is a pacemaker case.

8. A rate-responsive pacemaker system comprising:

pulsing means for providing pacing pulses at a controlled rate;

a first and a second unipolar lead coupled to said pulsing means and having a respective electrode adapted to couple said pulsing means to one of an atrium and a ventricle of a patient's heart respectively;

means for deriving a blood impedance signal by injecting selectively a current between one of said electrodes and a reference point and measuring the voltage across said other electrode and said reference point; and means for adjusting said controlled rate as a function of said impedance signal.

9. The rate-responsive pacemaker system of claim 8 wherein said one of said electrodes is provided for coupling to the atrium of the patient's heart.

10. The rate-responsive pacemaker system of claim 9 wherein said other of said electrodes is provided for coupling to the ventricle of the patient's heart.

11. The rate-responsive pacemaker system of claim 8 wherein said current is less than one milliamp.

12. The rate-responsive pacemaker system of claim 11 wherein said current is 0.1–2.0 milliamps.

13. The rate-responsive pacemaker system of claim 12 wherein said measuring current is applied in pulses of 1–50 microseconds.

14. The rate-responsive pacemaker system of claim 8 wherein said reference point in said pacemaker system is a pacemaker case.

15. A method of pacing a person's heart with a pacemaker system including a pulsing means for providing pacing pulses at a controlled rate, and a first and second unipolar leads, each having a respective electrode, one of said electrodes being secured to the atrium of said patient's heart and the other electrode being secured to the ventricle of the patient's heart, comprising the steps of:

injecting a current between one of said electrodes and a reference point;

measuring a voltage between the other of said electrodes and said reference point to determine an impedance; and adjusting said controlled rate in accordance with said impedance.

16. The method of claim 15 wherein said one electrode is attached to said atrium.

17. The method of claim 15 wherein said current is below a milliamp.

18. The method of claim 17 wherein said current is about 0.5 milliamps.

19. The method of claim 15 wherein said current is applied in pulses.

20. The method of claim 19 wherein each pulse has a duration of about 15 microseconds.

21. The method of claim 19 wherein said pulses are applied at a rate of 20 per second.

\* \* \* \* \*

UNITED STATES PATENT AND TRADEMARK OFFICE
CERTIFICATE OF CORRECTION

PATENT NO. : 5,562,712
DATED : October 8, 1996
INVENTOR(S) : Steinhaus, et al.

It is certified that error appears in the above-indentified patent and that said Letters Patent is hereby corrected as shown below:

Title page, item [75], change "Arker" to -- Parker --.

Signed and Sealed this

Twenty-first Day of January, 1997

Attest:

Attesting Officer

BRUCE LEHMAN

Commissioner of Patents and Trademarks